(12) United States Patent
Lillehei et al.

(10) Patent No.: US 8,795,149 B2
(45) Date of Patent: Aug. 5, 2014

(54) PNEUMATIC OR HYDRAULIC CARDIAC ASSIST DEVICES

(76) Inventors: Theodore J. Lillehei, Minneapolis, MN (US); Allan R. Robinson, Minneapolis, MN (US)

( * ) Notice: Subject to any disclaimer, the term of this patent is extended or adjusted under 35 U.S.C. 154(b) by 0 days.

(21) Appl. No.: 13/304,277

(22) Filed: Nov. 23, 2011

(65) Prior Publication Data

US 2012/0130485 A1 May 24, 2012

Related U.S. Application Data

(60) Provisional application No. 61/458,497, filed on Nov. 23, 2010.

(51) Int. Cl.
*A61N 1/362* (2006.01)
*A61M 1/10* (2006.01)

(52) U.S. Cl.
USPC .............................. 600/16; 623/3.21

(58) Field of Classification Search
USPC .................. 623/3.16, 3.2, 3.21; 600/16, 37
See application file for complete search history.

(56) References Cited

U.S. PATENT DOCUMENTS

| | | | |
|---|---|---|---|
| 5,607,385 A | 3/1997 | Francischelli | |
| 6,193,648 B1 | 2/2001 | Krueger | |
| 6,406,421 B1 | 6/2002 | Grandjean | |
| 6,595,912 B2 | 7/2003 | Lau | |
| 6,602,182 B1 * | 8/2003 | Milbocker | 600/16 |
| 6,896,652 B2 | 5/2005 | Alferness | |
| 7,097,611 B2 | 8/2006 | Lau | |
| 7,155,295 B2 | 12/2006 | Lau | |
| 7,198,594 B2 | 4/2007 | Shahinpoor | |
| 7,291,105 B2 | 11/2007 | Lau | |
| 7,381,181 B2 | 6/2008 | Lau | |
| 2003/0212306 A1 | 11/2003 | Banik | |
| 2004/0010180 A1 | 1/2004 | Scorvo | |
| 2004/0249236 A1 | 12/2004 | Hedge | |
| 2005/0004428 A1 | 1/2005 | Cox | |
| 2005/0255592 A1 | 11/2005 | Collins | |
| 2006/0142634 A1 | 6/2006 | Anstadt et al. | |
| 2006/0211909 A1 | 9/2006 | Anstadt | |
| 2007/0021652 A1 | 1/2007 | Lau et al. | |
| 2007/0197859 A1 | 8/2007 | Schaer et al. | |
| 2008/0116764 A1 | 5/2008 | Heim | |

OTHER PUBLICATIONS

Bar-Cohen, 2008, Electroactive polymer actuators and sensors. MRS Bulletin 33:173-177.
Smela, 2008, Conjugated polymer actuators. MRS Bulletin 33:197-204.
Park, 2008, Physical properties of ionic polymer-metal composites . . . MRS Bulletin 33:190-195.
Calvert, 2008, Gel Sensors and actuators. MRS Bulletin 33:207-212.
Taylor, DA. 1998, Regenerating functional myocardium, Nature Medicine 4:929-933.

* cited by examiner

*Primary Examiner* — Bruce E Snow
(74) *Attorney, Agent, or Firm* — Hugh McTavish

(57) ABSTRACT

The embodiments relate to cardiac assist devices that comprise a jacket that wraps the exterior of the heart, where the jacket comprises one or more pneumatic or hydraulic bladders. The pneumatic or hydraulic bladders are linked to a pump, and the pump fills the bladders with fluid and withdraws the fluid in a cycle to match beats of the heart to assist contraction and pumping of the heart in systole or to assist expansion and filling of the heart in diastole.

22 Claims, 7 Drawing Sheets

PNEUMATIC OR HYDRAULIC CARDIAC ASSIST DEVICES

This application claims priority under 35 U.S.C. §119(e) from U.S. provisional patent application Ser. No. 61/458,497, filed Nov. 23, 2010.

BACKGROUND

Congestive heart failure is a debilitating and progressive disease that causes a heart to pump less efficiently over time. Typically, the heart has been weakened by an underlying problem, such as clogged arteries, high blood pressure, a defect in heart muscles or heart valves, or some other medical condition. Many symptoms and conditions associated with heart failure can be treated, but to date in many cases the underlying impairment of the heart cannot.

One characteristic of heart failure is remodeling of the heart—that is, physical change to the size and shape of the heart and thickness of the heart wall. In many cases the wall of the left ventricle thins and stretches in places. The thinned portion of the myocardium is typically functionally impaired and other portions may grow or thicken to compensate.

Typically, the heart enlarges as heart failure progresses, which seems to be the result of the body trying to compensate for weakening heart muscles. The heart can become so enlarged that the heart can no longer provide an adequate supply of blood to the body. As a result, individuals afflicted with congestive heart failure often experience shortness of breath and fatigue even with minimal activity. Also, as the heart enlarges, the heart valves may not adequately close, which further reduces the heart's ability to supply blood to the body.

Drug therapies have been developed to treat individuals afflicted with congestive heart failure. A drug regimen of beta blockers, diuretics, and angiotensin-converting enzyme inhibitors (ACE inhibitors) aims to improve the effectiveness of the heart's contractions and slow CHF progression. Although drug therapy for heart failure can improve the quality of life and also modestly prolong survival, it is well established that many of the currently available approaches do not represent satisfactory long-term treatment options for a large number of patients.

Once the disease progresses to the point that medication is no longer effective, the currently preferred options are a heart transplant or a ventricular assist device (VAD). Approximately 550,000 new cases of CHF are diagnosed in the United States alone every year. Of these, at least 75,000 individuals are candidates for a heart transplant. But more than 50,000 men and women die every year waiting for a heart transplant because of a lack of donor hearts.

Only a few hundred VADs are implanted in the US each year. VAD use is limited because device implant surgery is highly invasive and complicated. Management of pump volume or pressure is difficult. VAD surgery adds insult to the heart because of the required surgical connections into the ventricle and aorta. But the largest contributor to complications from VAD implantation is the required direct interface of the device with the patient's blood. This can lead to clotting, strokes, and infection.

In addition to drugs, transplants, and VADs, heart failure has been treated with cardiac jackets or restraint devices. These basically consist of flexible material wrapped around the heart. A cardiac jacket is fitted around an enlarged heart to physically limit expansion of the heart during diastole. This may prevent further enlargement of the heart.

Improved methods and devices for treating heart failure and other cardiac diseases are needed.

SUMMARY

The embodiments relate to cardiac assist devices that comprise a jacket that wraps the exterior of the heart, where the jacket comprises one or more pneumatic or hydraulic bladders. The pneumatic or hydraulic bladders are linked to a pump, and the pump fills the bladders with fluid and withdraws the fluid in a cycle to match beats of the heart to assist contraction and pumping of the heart in systole or to assist expansion and filling of the heart in diastole.

The pneumatic or hydraulic fluid may be a gas or a liquid. In one embodiment, it is air. It may also be $O_2$, $N_2$, argon, or other suitable gas, or water, saline, or other suitable liquid.

One embodiment provides a device for treating cardiac disease comprising: (a) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define one chamber generally overlaying the right ventricle (the right chamber), or one chamber generally overlaying the left ventricle (the left chamber); (b) a first fluid passageway linked to the right chamber or the left chamber; (c) a fluid reservoir linked to the first fluid passageway; and (d) a pump linked to the fluid reservoir and adapted to pump fluid from the fluid reservoir into the right chamber or the left chamber and to withdraw the fluid from the chamber in a cycle to expand the right chamber or the left chamber during systole and contract the chambers during diastole to assist systolic pumping of the heart or diastolic refilling of the heart or both; wherein the chamber does not cover the apex of the heart and in operation the jacket does not compress the apex of the heart upward; wherein the chamber has an apical border toward the apex of the heart and below the widest point of the heart and a base border toward the base of the heart; wherein the fluid passageway is linked to the chamber near the apical border and below the widest point of the heart and the chamber expands and compresses the heart from near the apical border of the chamber toward the base border of the chamber.

Another embodiment provides a device for treating cardiac disease comprising: (a) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define (i) one chamber or a plurality of chambers collectively generally overlaying the right ventricle (the right chamber or chambers), and/or (ii) one chamber or a plurality of chambers collectively generally overlaying the left ventricle (the left chamber or chambers); (b) a first fluid passageway linked to the right chamber or chambers; (c) a second fluid passageway linked to the left chamber or chambers; (d) a fluid reservoir linked to the first and second fluid passageways; and (e) a pump linked to the fluid reservoir and adapted to pump fluid from the fluid reservoir into right chamber or chambers and the left chamber or chambers and to withdraw the fluid from the chambers in a cycle to expand the left chambers and/or the right chambers during systole and contract the chambers during diastole to assist systolic pumping of the heart or diastolic refilling of the heart or both; wherein the chambers do not cover the apex of the heart and in operation the jacket does not compress the apex of the heart upward; and wherein the one or more chambers overlaying the right ventricle are fluidically separated from the one or more chambers overlaying the left ventricle except through the fluid reservoir. Preferably the one or more chambers overlaying the left ventricle are delimited in part by a seam coupling the inner and outer layers and overlaying the anterior sulcus of the heart, and by a seam coupling the inner and outer layers and overlaying the posterior sulcus of the heart.

Another embodiment provides a system for treating heart disease comprising: (a) a device of the invention comprising a cardiac jacket and (b) a restraint jacket external to the cardiac jacket, the restraint jacket comprising a band of biocompatible material attached to an adjustable coupling mechanism, wherein the restraint jacket is adapted to be adjustable in circumference to restrain outward expansion of the cardiac jacket and to hold at least a portion of the cardiac jacket in a narrower circumference about the heart than it would be held without the restraint jacket, and wherein the restraint jacket is composed of flexible material.

Another embodiment provides a method of treating heart failure comprising: implanting a device of the invention or a system of the invention comprising a device of the invention in a mammalian patient, preferably a human, suffering from heart failure, and pumping fluid in the device with the pump to expand one or more chambers of the device and thereby assist pumping of the left ventricle and/or the right ventricle in the patient.

DETAILED DESCRIPTION

Figure 1:
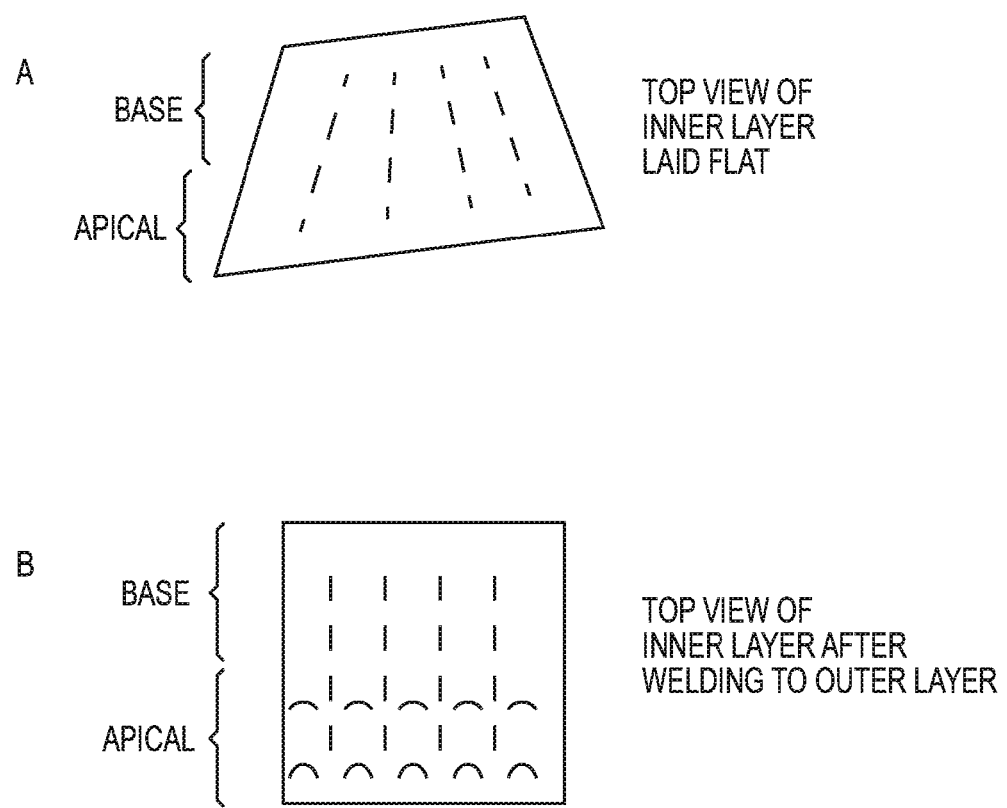
FIG. 1 is a schematic drawing of the inner layer of the cardiac jacket in some embodiments, showing the inner layer of the cardiac jacket as wider or baggier toward the apex and tighter or narrower toward the base.

One embodiment provides a device for treating cardiac disease comprising: first a cardiac jacket adapted to fit generally around the heart of a mammal, the jacket comprising an inner layer proximal to the heart and an outer layer distal to the heart, each layer composed of a biocompatible material, the inner and outer layers coupled to form one or more fluid-tight seals that define one chamber generally overlaying the right ventricle (the right chamber), or one chamber generally overlaying the left ventricle (the left chamber), or both the right chamber and the left chamber. Alternatively, the inner and outer layers can be coupled to form one or more fluid-tight seals that define a plurality of chambers that collectively generally overlay the right ventricle (the right chambers) or a plurality of chambers that collectively generally overlay the left ventricle (the left chambers), or both the right chambers and the left chambers. The device further comprises a fluid passageway linked to the right chamber or chambers or to the left chamber or chambers. The device further comprises a fluid reservoir linked to the fluid passageway; and a pump linked to the fluid reservoir and adapted to pump fluid from the fluid reservoir into the right chamber or chambers or the left chamber or chambers and to withdraw the fluid from the chambers in a cycle to expand the right chamber(s) or the left chamber(s) during systole and contract the chambers during diastole to assist systolic pumping of the heart or diastolic refilling of the heart or both.

In contraction, the device preferably should not compress the apex of the heart upward too much, because the apex is linked by the basingy fibers to the mitral valves and if the apex is raised it can lead to mitral regurgitation. Thus, preferably none of the chambers cover the apex of the heart. And preferably the jacket does not cover the apex of the heart. But some compression of the apex is permissible, provided it does not cause mitral regurgitation, so in some embodiments, the jacket covers the apex of the heart and in some embodiments, the device compresses the apex of the heart.

In one embodiment, the jacket has an apical border towards the apex of the heart and apical to the widest point of the heart and wherein the jacket does not overlay the apex of the heart.

The devices compress the left ventricle or right ventricle, or both, preferably from the below the widest point of the heart, near to the apical end, upward toward the base of the heart. To accomplish that in particular embodiments, the chamber has an apical border toward the apex of the heart and below the widest point of the heart and a base border toward the base of the heart; wherein the fluid passageway is linked to the chamber near the apical border and below the widest point of the heart and the chamber expands and compresses the heart from near the apical border of the chamber toward the base border of the chamber.

The term "apical" or "toward the apical end" refers to the direction toward the apex of the heart, which is basically lower in the body. The term "base border" means the border toward the base of the heart, which is basically upper in the body.

Where a plurality of chambers collectively overlay the right ventricle or the left ventricle, the plurality of chambers collectively have an apical border toward the apex of the heart and a base border toward the base of the heart; and the fluid passageway (or passageways) enter the chambers apical to the widest point of the heart.

Suitable hardware, including a hydraulic pump, a compliant reservoir and rotary mechanical valve, together with appropriate actuating electronics can all be implanted in the patient's body. If the power source is an internal battery, then power may be transcutaneously transmitted into the body to recharge this battery. Alternatively, the pump and power source may be outside the body. For instance, they may be held in a wearable vest. If the pump and power source are outside the body, a transcutaneous port is needed to transport the fluids of the system through the skin to and from the chambers of the cardiac jacket.

When the chambers are inflated, the heart is squeezed to assist systolic action. The chambers are deflated during diastolic action. If the walls of the chambers are directly or indirectly attached to the myocardium, deflation of the chambers may pull the walls outward and assist diastolic action. The walls of the chambers may be directly or indirectly attached to the myocardium by suturing a wall of the chamber to the myocardium or epicardium, or by an inner surface of the jacket that promotes tissue growth to attach to the jacket.

Diastolic action can also be assisted because of vacuum formed between the wall of the heart and the inner wall of the chambers, so that as the chambers deflate they pull the wall of the heart outward with them. Vacuum is more likely to form if the jacket is formed to fit closely to the contours of the heart.

The shape of the jacket preferably fits closely to the contours of the heart, in order to keep the jacket in place. It can be custom made for a particular patient based on the size and shape of that patient's heart, as determined by medical imaging. In other embodiments, one or more standard sizes of the jacket are used. The basal (upper) border of the jacket is preferably toward the base of the heart from the widest point of the heart and preferably has a smaller circumference than the widest point of the heart. Likewise, the apical border of the jacket is preferably toward the apex from the widest point of the heart and preferably has a smaller circumference than the widest point of the heart.

The device preferably does not compress either atrium of the heart.

Another embodiment provides a device for treating cardiac disease comprising: (a) a cardiac jacket adapted to fit generally around the heart of a mammal, the jacket comprising an inner layer proximal to the heart and an outer layer distal to the heart, each composed of a biocompatible material, the inner and outer layers coupled to form fluid-tight seals that define one chamber or a plurality of chambers collectively generally overlaying the right ventricle (the right chamber or chambers), and one chamber or a plurality of chambers collectively generally overlaying the left ventricle (the left chamber or chambers); (b) a first fluid passageway linked to the right chamber or chambers; (c) a second fluid passageway linked to the left chamber or chambers; (d) a fluid reservoir linked to the first and second fluid passageways; and (e) a pump linked to the fluid reservoir and adapted to pump fluid from the fluid reservoir into the right chamber or chambers and/or the left chamber or chambers and to withdraw the fluid from the chambers in a cycle to expand the left chambers and/or the right chambers during systole and contract the chambers during diastole to assist systolic pumping of the heart or diastolic refilling of the heart or both; wherein the chambers do not cover the apex of the heart and in operation the jacket does not compress the apex of the heart upward; wherein the one or more chambers overlaying the right ventricle are fluidically separated from the one or more chambers overlaying the left ventricle except through the fluid reservoir.

Figure 4:
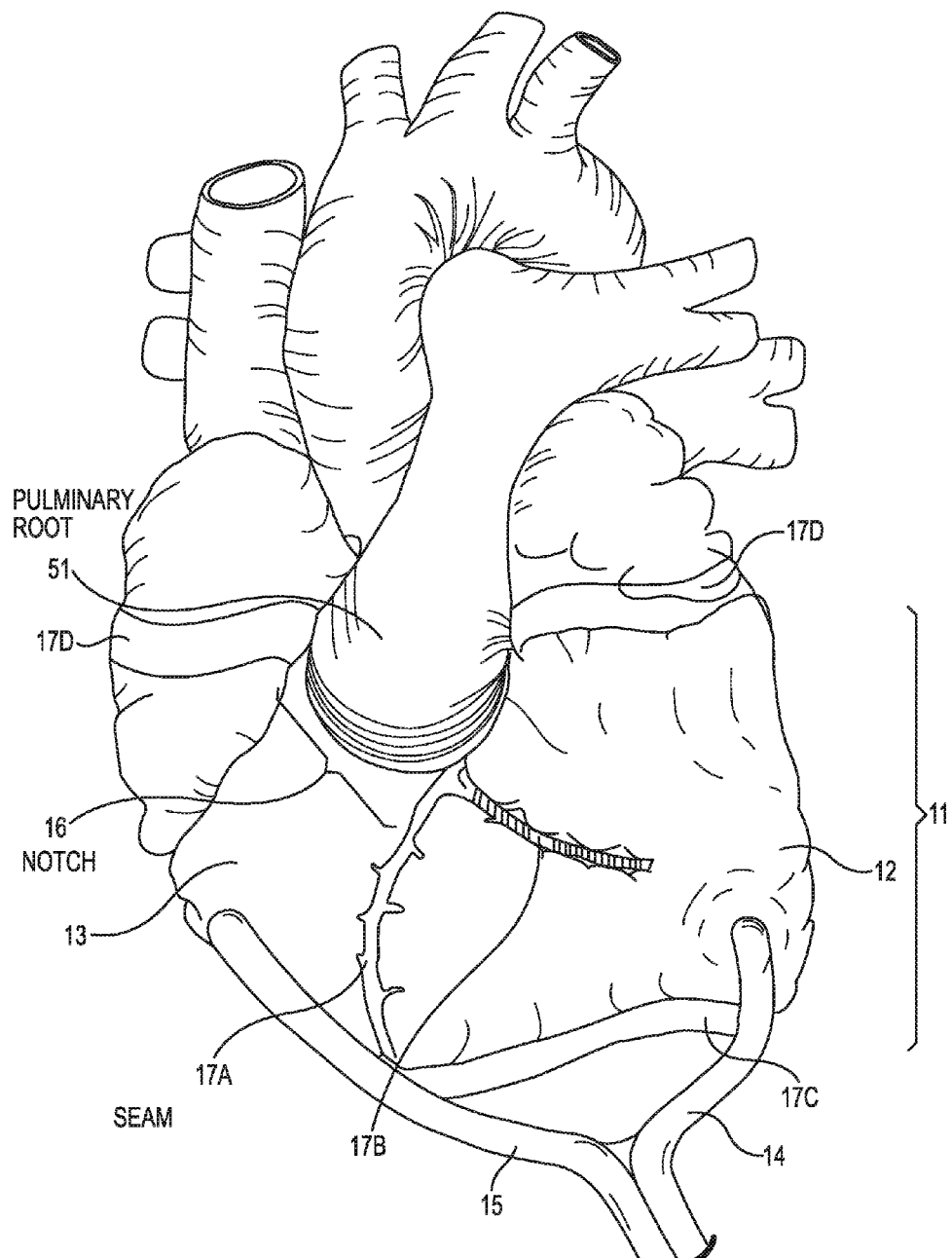
FIG. 4 shows one embodiment of a device of the invention comprising a cardiac jacket.

A jacket of the invention is shown in FIG. 4. Jacket 11 generally wraps around the heart. It includes left chamber 12 overlaying the left ventricle and right chamber 13 overlaying the right ventricle. Seams 17 are welds between an outer and an inner layer of material that make up the jacket. The lateral seam 17A in this anterior view overlays the anterior sulcus of the heart and divides the right chamber from the left chamber of the jacket. The jacket also has a seam 17C along the apical border of the jacket and a seam 17D along the base border of the jacket. Passageway 14 takes fluid from the pump and reservoir to and from the left chamber and passageway 15 takes fluid from the pump and the reservoir to and from the right chamber. The base border of the jacket includes a notch 16 around the pulmonary root 51.

Preferably the jackets of the invention, in addition to the chambers of the jacket, have an apical border towards the apex of the heart and below the widest point of the heart and the jacket does not overlay the apex of the heart.

The device with one or more chambers generally overlaying the right ventricle and one or more chambers generally overlaying the left ventricle in specific embodiments is adapted to separately control fluid flow into the right chamber(s) as compared to fluid flow into the left chamber(s) to modulate assistance separately to the left ventricle and the right ventricle. Thus, fluid flow to the left and right chambers can be separately controlled or adjusted, e.g., by valves.

Congestive heart failure patients and other heart patients may have more damage to one ventricle than to the other. In these cases, it may be important to only compress the more damaged of the ventricles or to differentially tailor the pressure exerted on each ventricle. With the chamber(s) overlaying the left ventricle fluidically separated from the chamber(s) overlaying the left ventricle, and with each chamber specific for one ventricle, and with separate fluid passageways to the left and right chambers, it is possible to alter the amount of fluid that goes toward compressing the left ventricle as compared to the right ventricle. If only the left ventricle is impaired, only the left chambers might be filled. Alternatively, both ventricles may be compressed, but the amount of fluid flowing into the left and right chambers of the jacket may be tailored to fit the particular needs of the patient. This may be done, e.g., by valves separately controlling fluid flow into the left and right fluid passageways.

In one embodiment, the chambers of the cardiac jacket consist of one chamber generally overlaying the right ventricle and/or one chamber generally overlaying the left ventricle.

In one embodiment, the first and second fluid passageways enter the chambers apical to the widest point of the heart. Preferably, the device squeezes the heart from the apical end toward the base in such as manner as to "scoop" blood upward in the ventricles. Having the fluid passageways enter near the apical edge of the chambers or the jacket helps to achieve this because it causes the chambers to expand first near the apical edge.

Figure 2:
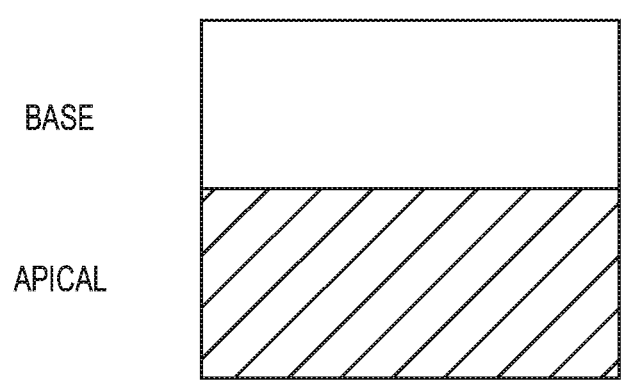
FIG. 2 is a schematic drawing of the inner layer of the cardiac jacket in some embodiments, showing the inner layer of the cardiac jacket as thinner or more expandable toward the apex and thicker or less expandable toward the base.

In one embodiment, the device is adapted to squeeze the left ventricle and/or the right ventricle from the apical end toward the base. To achieve this, as noted above, it is helpful to have the fluid passageways enter the chambers near the apical end of the chambers or near the apical border of the jacket. In other embodiments, the inner layer of the jacket (which is the inner layer of the chambers) may be composed of a variable thickness of material. This is shown in FIG. 2, where the apical region of the inner layer (shown as shaded) of the chambers is more expandable than the base region of the inner layer (shown without shading). Thus, when fluid fills the chamber, the apical region will expand more easily and thus expand faster than the base region, and squeezing the heart will begin at the apical region. In some embodiments, rather than two distinct regions, the expandability of the material in the inner layer may be in a gradient with highest expandability near the apex and lower toward the base.

Similarly, in FIG. 1, the apical region of the inner layer of the chambers is wider than the outer layer when laid flat (panel A), but when welded to the outer layers is welded at the same width in the apical and base regions (panel B). Thus, the apical region is looser and can expand more easily when fluid flows into the chamber. This allows it to expand first near the apical border and then toward the base border.

Figure 3:
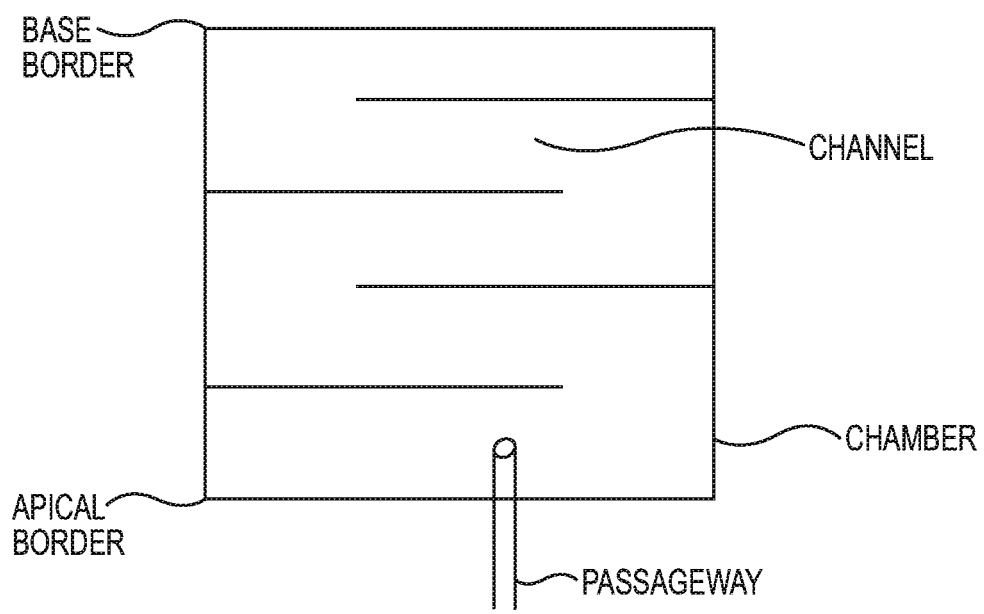
FIG. 3 shows a chamber of the cardiac jacket in some embodiments laid flat showing passageways through the chamber that direct fluid flow from the apical border toward the base border to expand the chamber from the apical border toward the base border.

In a preferred embodiment, the inner layer need not be looser near the apical border or thinner or more flexible near the apical border than near the base border. Rather, squeezing the heart first near the apical border of the jacket and then moving the pressure toward the base border of the jacket is achieved by having channels within the right and/or left chambers as shown in FIG. 3. The passageway that feeds fluid to the chamber links to the chamber near the apical border, and thus fluid first flows into and expands the channels within the chamber near the apical border and then flows upward through the channels toward the base border. In this way, the device scoops blood from the lower or apical regions of the ventricle upward toward the aorta in the left ventricle or pulmonary artery in the right ventricle near the upper end of the ventricles.

The inner layer of the chambers should preferably be more expandable than the outer layer, so that expansion presses against and squeezes the heart wall. But the jacket may have the inner and outer layers of the chamber or chambers be the same material and equally expandable. The inner and outer layers may be differentially expandable by being composed of different materials and/or different thicknesses of materials. They also can have different amounts of expandability by making the inner layer a larger area than the outer layer, when laid flat, so that the inner layer is "baggier" and can expand more. In a preferred embodiment, the inner layer and outer layer are both ELASTEON, a polyurethane from Aortech Corp., but the inner layer is thinner and more expandable than the outer layer. Thus, the expansion with fluid filling is predominantly inward, toward the heart wall. In one embodiment we have made, the inner and outer layers are both identical medical grade polyurethanes, and the outer layer is thicker than the inner layer by a ratio of 7.5:4.

Thus, in a specific embodiment, the inner layer of the chamber or chambers is elastic and is more easily stretched than the outer layer of the jacket.

In particular embodiments, the inner and outer layers are composed of biocompatible material, and the biocompatible material is or comprises a silicone, a polyurethane, or a silicone/urethane copolymer.

In a particular embodiment, the outer layer comprises a mesh layer. The mesh layer may be on the inner surface of the outer layer, on the outer surface of the outer layer, or in a sandwich between two continuous layers of material that together with the mesh layer form the outer layer. The mesh is flexible. In a particular embodiment it is the a hernia mesh, i.e., a mesh material that is used to surgically repair hernias. The mesh is preferably a biocompatible material. It is used to strengthen the outer layer of the chamber to make the outer layer less expandable than the inner layer, so when fluid is pumped into the chamber, most of the expansion is of the inner layer and thus the expansion is directed inward to squeeze the left and/or right ventricles of the heart. A mesh is used because it adds strength but is more flexible than a continuous layer of material would be.

In one embodiment of the device, the device does not further comprise a rigid shell surrounding the cardiac jacket and restraining outward expansion of the cardiac jacket.

Where there is one left chamber and one right chamber, the borders of the chambers should match the upper and lateral borders of the ventricles. The lateral (or side) borders are the anterior sulcus and posterior sulcus. The upper border is the atrialventricular ring. Thus, in one embodiment, the left chamber is delimited in part by a seam coupling the inner and outer layers and overlapping the anterior sulcus of the heart (seam 17A in FIG. 4) and a second seam coupling the inner and outer layers and overlaying the posterior sulcus of the heart. Where a plurality of chambers collectively overlay the left ventricle, the plurality of chambers may be delimited in part by a first seam coupling the inner and outer layers and overlapping the anterior sulcus of the heart and a second seam coupling the inner and outer layers and overlaying the posterior sulcus of the heart.

In one embodiment, the right chamber is delimited in part by a first seam coupling the inner and outer layers and overlapping the anterior sulcus of the heart and a second seam coupling the inner and outer layers and overlaying the posterior sulcus of the heart. Where a plurality of chambers collectively overlay the right ventricle, the plurality of chambers may be delimited in part by a first seam coupling the inner and outer layers and overlapping the anterior sulcus of the heart and a second seam coupling the inner and outer layers and overlaying the posterior sulcus of the heart.

In one embodiment, the left chamber is delimited in part by a seam coupling the inner and outer layers and overlapping the atrialventricular ring of the heart (seam 17D in FIG. 4). Where a plurality of chambers collectively overlay the left ventricle, the plurality of chambers may be delimited in part by a seam coupling the inner and outer layers and overlapping the atrialventricular ring of the heart.

In one embodiment, the right chamber is delimited in part by a seam coupling the inner and outer layers and overlapping the atrialventricular ring of the heart. Where a plurality of chambers collectively overlay the right ventricle, the plurality of chambers may be delimited in part by a seam coupling the inner and outer layers and overlapping the atrialventricular ring of the heart.

In one embodiment, the inner and outer layers of the chambers are composed of polymer. In this case, the seams or couplings that form fluid-tight seals that define the chambers may be welds, e.g., thermal welds or sonic welds.

The jacket is preferably formed so the upper border of the jacket is above the widest point of the heart. As mentioned above, a good position for the upper border of the jacket or chambers is the atrialventricular ring. The lower border of the jacket or chambers in some embodiments is about 25-33% of the distance from the apex to the atrialventricular ring (i.e., closer to the apex and below the widest point of the heart).

In a preferred embodiment, the base border of the jacket forms a notch that generally conforms to the pulmonary artery, as shown by notch 16 in FIG. 4.

The device can be customized for a particular patient. Heart size and shape varies between particular persons—in particular, diseased hearts vary in size and shape. Thus, the size and shape of the jacket is ideally customized for a particular patient.

Seams between chambers do not expand or expand less than other areas, and where a chamber has inner seams, e.g., to form channels within the chamber, these do not expand or expand less than other areas. Thus, different areas of the chamber expand more than other areas. Likewise, different areas of the heart of a patient have been damaged more than other areas. For instance, a myocardial infarction causes damage to a particular section of the myocardium. In some embodiments of jacket designs, more pressure is exerted on particular areas of the wall of a chamber than other areas of the same chamber. It may be desirable to compress relatively healthy areas more than damaged areas or vice versa. Where the damage is old and has developed scarring and stiffness, it may be desirable to compress and move the damaged areas more than the healthy areas. In other cases, for instance in some cases where the damage is new and still healing, it may be desirable to not compress the damaged areas but to exert most of the compression on healthier areas of the ventricle. If more compression is desired on a damaged area than healthy areas, with customized jackets, a seam should overlay a comparatively healthy area of the heart and areas of greatest expansion in the chamber should overlay a comparatively damaged area. In FIG. 4, seam 17B is within the left chamber and does not separate chambers. In a custom made jacket, the location of this seam may be placed over a comparatively healthy area of the heart, while open areas of the left chamber 12 may be placed over a comparatively damaged area of the left ventricle.

Thus, in one embodiment, the device is customized for a particular patient, and the one or more chambers overlaying the left ventricle comprise a seam that does not expand and the seam overlays a comparatively healthy area of the wall of the left ventricle of the patient, and the one or more chambers comprises an area of greater expansion that overlays a comparatively damaged area of the left ventricle of the patient. In a particular embodiment, the comparatively damaged area is an area of a myocardial infarction. The same can be done with the right chamber and the right ventricle. The damaged areas can be identified by methods known to persons of skill in the art, including echocardiogram, PET scan, perfusion scan, and MRI.

Thus, in one embodiment, the device is customized to compress healthy and diseased or damaged myocardium differently.

Figure 5:
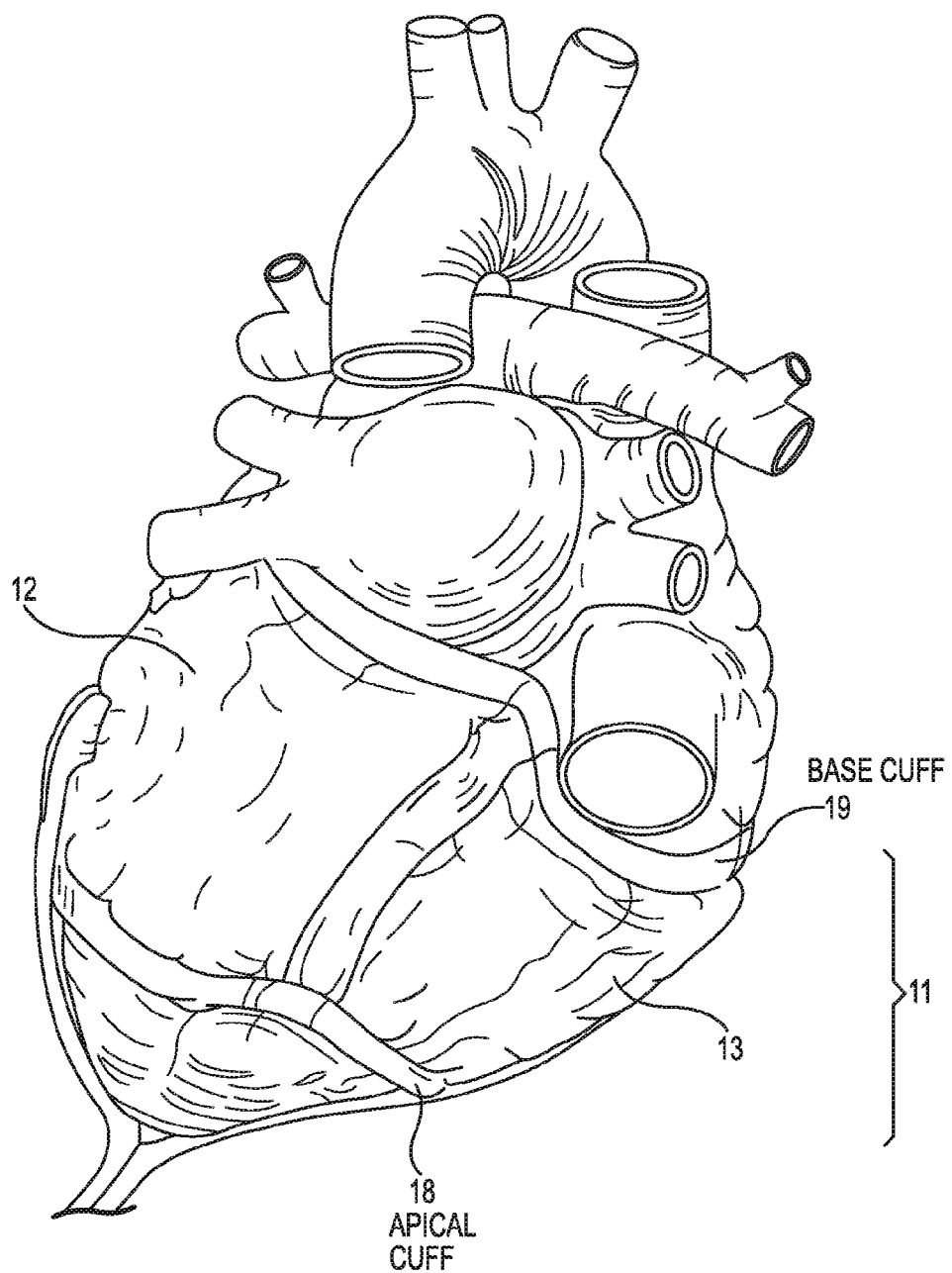
FIG. 5 shows another embodiment of a device of the invention comprising a cardiac jacket.

In another embodiment, the jacket has drawstrings at its top and/or bottom borders to manually adjust the fit to fit a patient's heart. In this embodiment, the jacket has an apical border toward the apex of the heart and a base border toward the base of the heart and the jacket does not cover the apex of the heart, wherein the apical border or the base border of the jacket includes a cuff forming a passageway along the border and includes an adjustable drawstring passing through the cuff that can be adjusted in circumference and fastened at a particular circumference fitting the heart of the patient. In a particular embodiment, the drawstring comprises a hook-and-loop fastening mechanism. Many materials can be molded into hook-and-loop mechanism. For instance the drawstring can be a biocompatible polyurethane and the hook-and-loop fastening mechanism can be the same material. This is shown in FIG. 5 where cuff 18 along the apical border may include an inner drawstring (not shown). Likewise, cuff 19 along the base border of the jacket may include an inner drawstring as well as or instead of the apical border.

In another embodiment of the devices, the device comprises a computerized generator electrically linked to the pump to control the pump and electrically linked to one or more sensing and/or pacing electrodes electrically coupled to the heart.

In one embodiment, the electrodes are sensing electrodes wherein the device is adapted to detect contraction rhythm of the heart with the sensing electrodes and to generate electrical signals effective to control the pump at a variable rate responsive to physiological activity of the mammal. The device is preferably adapted to begin expanding the chamber or chambers of the jacket in synchrony with an electrocardiogram phase detected in the heart, for instance, when the heart is in a QR electrocardiogram phase.

In another embodiment, the electrodes are pacing electrodes and the device paces pumping of the heart muscle. Of course, the device can also comprise an adjustable rate pacemaker, where it comprises combined sensing and pacing electrodes or both sensing and pacing electrodes.

Figure 6:
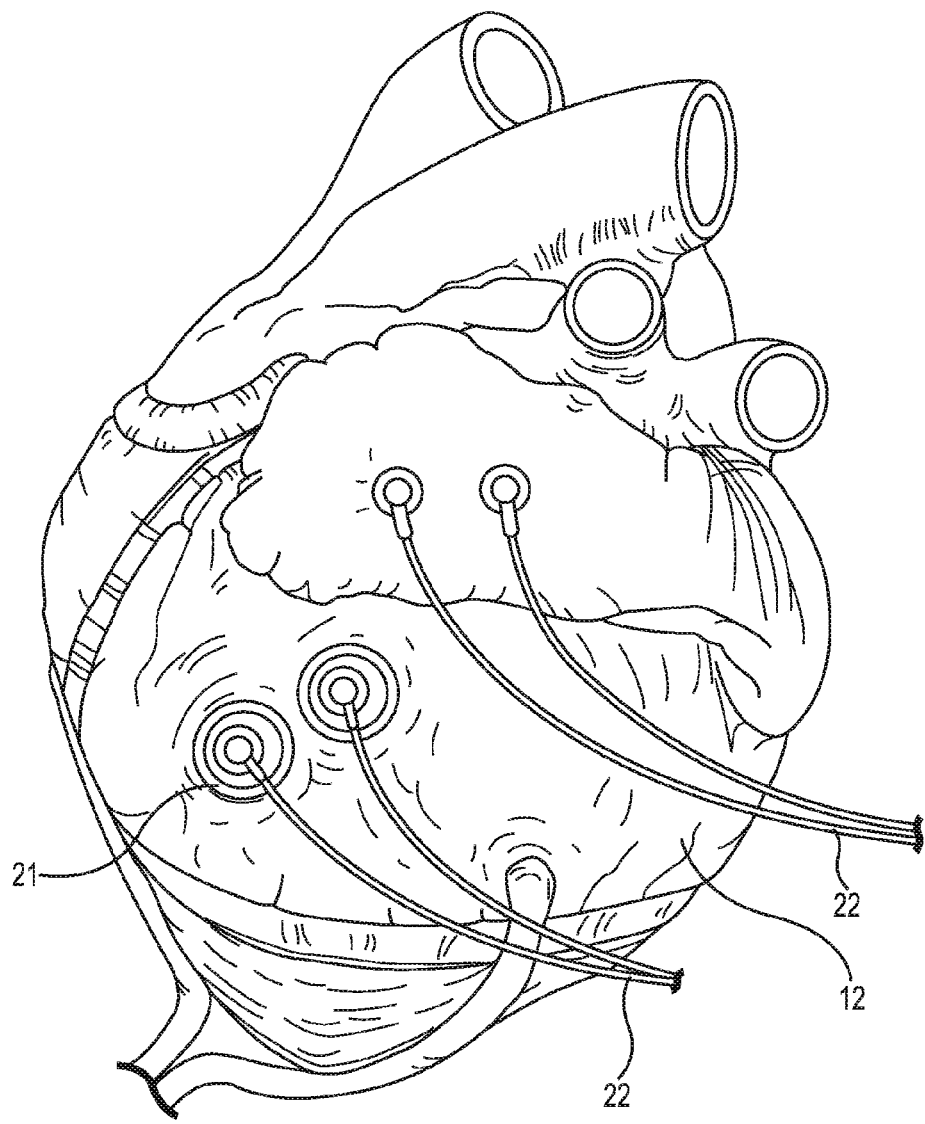
FIG. 6 shows another embodiment of a device of the invention comprising electrodes passing through conduits in the jacket to contact the heart.

In a specific embodiment of the device, one or more chambers of the jacket have an outer surface distal to the heart and an inner surface proximal to the heart, wherein the inner and/or outer layers of the chamber form one or more conduits through the chamber from the outer surface through the inner surface, wherein the conduits are exterior to the chamber; and wherein the electrodes pass through the conduits to contact the heart. To explain, the chamber can have a donut configuration with a hole in the middle through which electrodes can pass. This is shown in FIG. 6, where conduits 21 in the left chamber 12 allow electrodes 22 to pass through the jacket to directly contact the heart.

In another embodiment, the inner layer of the jacket is contoured to form one or more channels raised above the surface of the heart, wherein the electrodes pass through the channels to contact the heart. In this way, the chambers do not directly contact the electrodes or do not press against the electrodes when the chambers expand.

Another embodiment of the invention provides a system for treating heart disease comprising: (a) a device comprising: (i) a cardiac jacket adapted to fit generally around the heart of a mammal, the jacket comprising an inner layer proximal to the heart and an outer layer distal to the heart, each composed of a biocompatible material, the inner and outer layers coupled to form fluid-tight seals that define one chamber generally overlaying the right ventricle (the right chamber), or one chamber generally overlaying the left ventricle (the left chamber); (ii) a first fluid passageway linked to the right chamber or the left chamber; (iii) a fluid reservoir linked to the first fluid passageway; and (iv) a pump linked to the fluid reservoir and adapted to pump fluid from the fluid reservoir into the right chamber or the left chamber and to withdraw the fluid from the chambers in a cycle to expand the right chamber or the left chamber during systole and contract the chambers during diastole to assist systolic pumping of the heart or diastolic refilling of the heart or both. The chamber does not cover the apex of the heart and in operation the jacket does not compress the apex of the heart upward. The chamber has an apical border toward the apex of the heart and below the widest point of the heart and a base border toward the base of the heart; wherein the fluid passageway is linked to the chamber near the apical border and below the widest point of the heart and the chamber expands and compresses the heart from near the apical border of the chamber toward the base border of the chamber. The system further comprises (b) a restraint jacket external to the cardiac jacket, the restraint jacket comprising a band of biocompatible material attached to an adjustable coupling mechanism, wherein the restraint jacket is adapted to be adjustable in circumference to restrain outward expansion of the cardiac jacket and to hold at least a portion of the cardiac jacket in a narrower circumference about the heart than it would be held without the restraint jacket.

Figure 7:
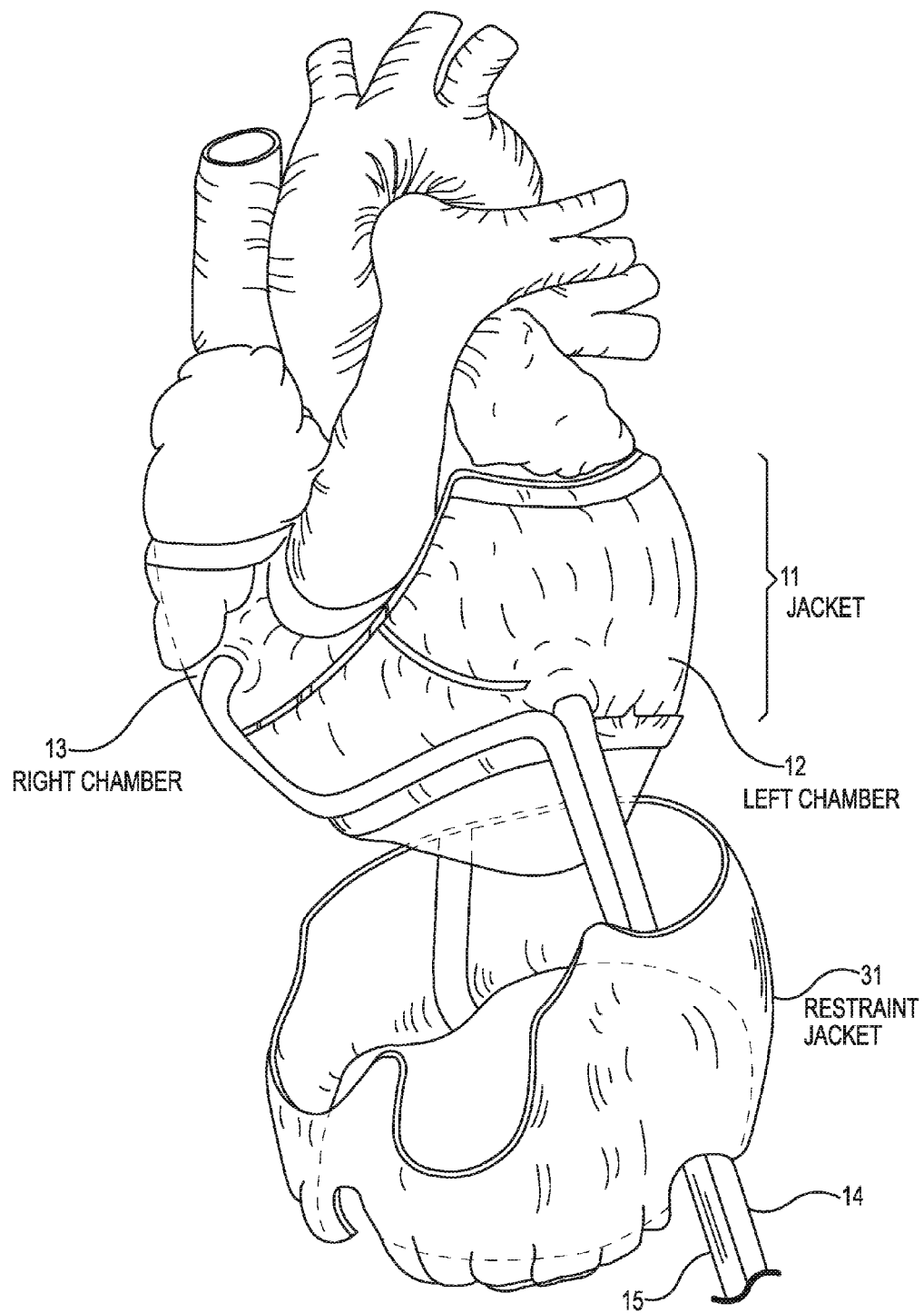
FIG. 7 shows an embodiment with a cardiac jacket 11 and a restraint jacket 31.

A restraint jacket 31 is shown in FIG. 7. It may be raised to overlay cardiac jacket 11.

Use of the restraint jacket in some cases gives firmer control of expansion, so nearly all the expansion of the chambers is directed inward toward the heart, rather than both inward and outward (away from the heart). The restraint jacket also allows one to use a cardiac jacket that is more standardized. The restraint jacket can be adjusted with its adjustable coupling mechanism to fit the heart and constrain a standardized sized cardiac jacket. Thus, the system with the restraint jacket may be especially suitable in emergency situations, where there is not time to manufacture a customized cardiac jacket for the patient. However, it is also usable in all situations, including with a custom-sized cardiac jacket. An advantage of the restraint jacket is that it provides more restraint against outward expansion of the chambers than would otherwise be possible. Thus, it helps to force expansion of the chambers inward, where the expansion productively helps pump the heart.

Optionally, the restraint jacket does not include drawstrings along its cuffs and is not adjustable. It may be made in several standard sizes for different users or customized for a particular patient.

The coupling mechanism of the restraint jacket may be any suitable coupling mechanism. In one embodiment it may be a hook-and-loop mechanism. In another embodiment, the coupling mechanism is a knot, which can be manually tied by the surgeon.

Another embodiment provides a method of treating heart failure comprising: implanting a device or system of the invention in a patient suffering from heart failure, and pumping fluid in the device with the pump to expand one or more chambers of the device and thereby assist pumping of the left ventricle and/or the right ventricle in the patient.

In a particular embodiment, the patient is suffering from heart failure secondary to myocarditis or traumatic cardiac injury. These are temporary conditions, and patients need assistance only until they recover from the condition. At that point, the device can be removed or turned off.

An advantage of the devices of the invention over conventional left ventricular assist devices (LVADs) is that LVADs require creating an opening in the heart wall to allow blood to flow into the LVAD. Conventional LVADs have a tube passing through the wall of the left ventricle, and another tube passing through the wall of the aorta, and a pump linking the two tubes. This requires placing a hole in the heart, which traumatizes an already damaged heart. Although some LVADs are used temporarily, this surgical damage to the heart makes it more difficult for the heart to recover from a temporary condition such as myocarditis or traumatic cardiac injury and more difficult to remove the LVAD. In contrast, the devices of the invention are placed over the heart without damaging the heart. They can be implanted and removed without damaging the heart. This makes them particularly well suited for treating temporary conditions.

Another key advantage of the present devices over conventional LVADs is that the present devices have no blood contact. Conventional LVADs are based on passing blood through artificial tubing and an artificial pump. The blood is constantly contacting artificial materials, which provide surfaces for clotting and damage to blood cells. Conventional LVADs therefore require that the patient be placed on anticoagulant therapy; the devices of the present invention do not.

Also, with a conventional LVAD the patient is entirely dependent on it for pumping the blood. If the LVAD fails, the patient dies almost immediately. With the present devices, if the device were to fail, the patient would be no worse off than he was before the device was implanted. His own heart would continue to pump, just without assistance from the device.

There are several ways the devices of the invention can be used. The chambers can inflate and the device assist pumping in systole with every beat of the heart. But it can also be used to assist only every 2nd beat, every 3rd beat, or every 4th beat. Alternatively, for some patients it might be used only at nighttime during sleep. The patient could then remove the external power pack, if the device uses an external power pack, and be free of it during the day, if he or she only needs assistance part of the day. For many patients, it may be useful to gradually wean the patient from the device. Thus, the device may initially assist with every beat all day, and then over time it could shift to assisting with only every other beat or only at night or only during the day.

The devices and cardiac jackets of the devices are preferably adapted to contour to the heart wall as the heart squeezes. This is accomplished by contouring of the inner wall of the one or more chambers or by making the inner wall of the chambers flexible enough that the inner wall conforms itself to the wall of the heart as the heart constricts and expands. In this way, the device follows the helical squeezing pattern of the heart. See, for example, www.helicalheart.com and Torrent-Guasp F et al, Towards new understanding of the heart structure and function, *Eur. J. Cardiothorac. Surg.* 2005, 27(2):191-201.

In some embodiments, system comprises an active cardiac jacket as described herein, with one or more chambers that inflate and deflate to assist the heart, and an inactive inner liner that wraps the heart and lies proximal to the heart from the cardiac jacket. The inner liner helps to reduce abrasion or friction on the myocardium that might arise from the squeezing of the active cardiac jacket. Optionally, the system can also include a restraint jacket, distal to the heart from the cardiac jacket, as is described herein, in addition to the inactive inner liner.

The inner liner is composed of a biocompatible material. In specific embodiments, it comprises polyurethane, a polyurethane/silicone copolymer or polymer mixture, or collagen, or a polyurethane/collagen copolymer.

The devices are designed to compress enough to assist with pumping of the heart, but not so much as to close coronary arteries or veins and interfere with coronary blood flow. Coronary blood flow, however, is primarily during diastole, while compression by the devices is during systole, which lessens problems with partially or fully closing coronary arteries or veins.

As will be noted, these devices are adaptable to diffentially compress one ventricle or another, and to differentially compress particular areas of the wall of a particular ventricle, e.g., compress healthy tissue more or less than scarred or damaged tissue. Likewise, the devices may temporally compress one ventricle or one area of the heart before another. For instance, the compression can go sequentially from the apex to the base, so as to pump blood upward in the ventricle being compressed.

All patents, patent documents, and non-patent references cited are hereby incorporated by reference.

What is claimed is:

1. A device for treating cardiac disease comprising:
  a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define one chamber adapted to generally overlay the right ventricle (the right chamber), or one chamber adapted to generally overlay the left ventricle (the left chamber);
  a first fluid passageway linked to the right chamber or the left chamber;
  a fluid reservoir linked to the first fluid passageway; and
  a pump linked to the fluid reservoir and adapted to pump fluid from the fluid reservoir into the right chamber or the left chamber and to withdraw the fluid from the chamber in a cycle to expand the right chamber or the left chamber during systole and contract the chambers during diastole to assist systolic pumping of the heart or diastolic refilling of the heart or both;
  wherein the chamber in use does not cover the apex of the heart and in operation the jacket does not compress the apex of the heart upward;
  wherein the chamber has an apical border that in use is toward the apex of the heart and below the widest point of the heart and a base border that in use is toward the base of the heart; wherein the fluid passageway is linked to the chamber near the apical border and below the widest point of the heart and the chamber in use expands and compresses the heart from near the apical border of the chamber toward the base border of the chamber;

wherein at least one of the chambers comprises internal seals that form channels through the chamber and slow fluid flow through the chamber compared to an otherwise identical chamber lacking the internal seals and wherein the channels serve to channel incoming fluid flow from the apical border of the chamber toward the base border of the chamber.

2. The device of claim 1 wherein the device is customized for a particular patient, and the chamber comprises a seam that does not expand and the seam is adapted to overlay a comparatively healthy area of the wall of the left or right ventricle of the ventricle of the patient, and the chamber comprises an area of greater expansion that is adapted to overlay a comparatively damaged area of the left or right ventricle of the patient.

3. The device of claim 1 wherein the device is customized for a particular patient, and the chamber comprises a seam that does not expand and the seam is adapted to overlay a comparatively damaged area of the wall of the left or right ventricle of the patient, and the one or more chambers comprises an area of greater expansion that is adapted to overlay a comparatively healthy area of the left or right ventricle of the patient.

4. The device of claim 3 wherein the comparatively damaged area is the location of a myocardial infarction.

5. A device for treating cardiac disease comprising:
a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define one chamber adapted to generally overlay the right ventricle (the right chamber), or one chamber adapted to generally overlay the left ventricle (the left chamber);
a first fluid passageway linked to the right chamber or the left chamber;
a fluid reservoir linked to the first fluid passageway; and
a pump linked to the fluid reservoir and adapted to pump fluid from the fluid reservoir into the right chamber or the left chamber and to withdraw the fluid from the chamber in a cycle to expand the right chamber or the left chamber during systole and contract the chambers during diastole to assist systolic pumping of the heart or diastolic refilling of the heart or both;
wherein the chamber in use does not cover the apex of the heart and in operation the jacket does not compress the apex of the heart upward;
wherein the chamber has an apical border that in use is toward the apex of the heart and below the widest point of the heart and a base border that in use is toward the base of the heart; wherein the fluid passageway is linked to the chamber near the apical border and below the widest point of the heart and the chamber in use expands and compresses the heart from near the apical border of the chamber toward the base border of the chamber;
wherein the jacket has an apical border that in use is toward the apex of the heart and a base border that in use is toward the base of the heart and the jacket does not cover the apex of the heart, wherein the apical border or the base border of the jacket includes a cuff forming a passageway along the border and includes an adjustable drawstring passing through the cuff that can be adjusted in circumference and fastened at a particular circumference fitting the heart of the patient.

6. A device for treating cardiac disease comprising:
a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define one chamber adapted to generally overlay the right ventricle (the right chamber), or one chamber adapted to generally overlay the left ventricle (the left chamber);
a first fluid passageway linked to the right chamber or the left chamber;
a fluid reservoir linked to the first fluid passageway; and
a pump linked to the fluid reservoir and adapted to pump fluid from the fluid reservoir into the right chamber or the left chamber and to withdraw the fluid from the chamber in a cycle to expand the right chamber or the left chamber during systole and contract the chambers during diastole to assist systolic pumping of the heart or diastolic refilling of the heart or both;
wherein the chamber in use does not cover the apex of the heart and in operation the jacket does not compress the apex of the heart upward;
wherein the chamber has an apical border that in use is toward the apex of the heart and below the widest point of the heart and a base border that in use is toward the base of the heart; wherein the fluid passageway is linked to the chamber near the apical border and below the widest point of the heart and the chamber in use expands and compresses the heart from near the apical border of the chamber toward the base border of the chamber;
wherein the base border of the jacket is adapted to overlay the atrialventricular ring of the heart.

7. The device of claim 6 wherein the cardiac jacket comprises both a left chamber and a right chamber.

8. The device of claim 6 further comprising:
a computerized generator electrically linked to the pump to control the pump and electrically linked to one or more sensing and/or pacing electrodes adapted to be electrically coupled to the heart.

9. The device of claim 8 wherein the chamber or chambers have an outer surface distal to the heart and an inner surface proximal to the heart, wherein the inner and outer layers of at least one of the chambers form one or more conduits through the chamber from the outer surface through the inner surface, wherein the conduits are exterior to the chamber; and wherein in use the electrodes pass through the conduits to contact the heart.

10. The device of claim 6 wherein the inner layer of the jacket is elastic and is more easily stretched than the outer layer of the jacket.

11. The device of claim 6 wherein the outer layer of the jacket comprises a flexible mesh that decreases the expandability of the outer layer.

12. The device of claim 6 wherein the base border of the jacket forms a notch that generally conforms to the root of the pulmonary artery.

13. The device of claim 6 wherein the device does not further comprise a rigid shell surrounding the cardiac jacket and restraining outward expansion of the cardiac jacket.

14. The device of claim 6 further comprising a restraint jacket external to the cardiac jacket, the restraint jacket comprising a band of biocompatible material attached to an adjustable coupling mechanism, wherein the restraint jacket is adapted to be adjustable in circumference to restrain outward expansion of the cardiac jacket and to hold at least a portion of the cardiac jacket in a narrower circumference about the heart than it would be held without the restraint jacket, and wherein the restraint jacket is composed of flexible material.

15. A method of treating heart failure comprising:
implanting the device of claim 6 in a mammalian patient suffering from heart failure, and
pumping fluid in the device with the pump to expand one or more chambers of the device and thereby assist pumping of the left ventricle and/or the right ventricle in the patient.

16. The method of claim 15 wherein the patient is suffering from heart failure secondary to myocarditis or traumatic cardiac injury.

17. The method of claim 16 wherein the method further comprises removing the device after the patient has recovered.

18. A device for treating cardiac disease comprising:
(a) a cardiac jacket adapted to fit generally around the heart of a mammal, the jacket comprising an inner layer proximal to the heart and an outer layer distal to the heart, each composed of a biocompatible material, the inner and outer layers coupled to form one or more fluid-tight seals that define (i) one chamber or a plurality of chambers adapted to collectively generally overlay the right ventricle (the right chamber or chambers), and (ii) one chamber or a plurality of chambers adapted to collectively generally overlay the left ventricle (the left chamber or chambers);
(b) a first fluid passageway linked to the right chamber or chambers;
(c) a second fluid passageway linked to the left chamber or chambers;
(d) a fluid reservoir linked to the first and second fluid passageways; and
(e) a pump linked to the fluid reservoir and adapted to pump fluid from the fluid reservoir into the right chamber or chambers and the left chamber or chambers and to withdraw the fluid from the chambers in a cycle to expand the left chambers and/or the right chambers during systole and contract the chambers during diastole to assist systolic pumping of the heart or diastolic refilling of the heart or both;
wherein the chambers in use do not cover the apex of the heart and in operation the jacket does not compress the apex of the heart upward;
wherein the one or more chambers adapted to overlay the right ventricle are fluidically separated from the one or more chambers adapted to overlay the left ventricle except through the fluid reservoir;
wherein the one or more chambers adapted to overlay the left ventricle are delimited in part by a seam coupling the inner and outer layers and adapted to overlay the anterior sulcus of the heart, and by a seam coupling the inner and outer layers and adapted to overlay the posterior sulcus of the heart;
wherein the right chamber or chambers and the left or chambers collectively have an apical border that in use is toward the apex of the heart and below the widest point of the heart and a base border that in use is toward the base of the heart;
wherein the base border of the jacket is adapted to overlay the atrialventricular ring of the heart.

19. The device of claim 18 wherein the base border of the jacket forms a notch that generally conforms to the root of the pulmonary artery.

20. A method of treating heart failure comprising:
implanting the device of claim 18 in a mammalian patient suffering from heart failure, and
pumping fluid in the device with the pump to expand one or more chambers of the device and thereby assist pumping of the left ventricle and/or the right ventricle in the patient.

21. The method of claim 20 wherein the patient is suffering from heart failure secondary to myocarditis or traumatic cardiac injury.

22. The method of claim 21 wherein the method further comprises removing the device after the patient has recovered.

* * * * *